(12) United States Patent
Niazi

(10) Patent No.: US 12,280,092 B2
(45) Date of Patent: Apr. 22, 2025

(54) REPROGRAMMED T CELL-LIKE NK CELLS

(71) Applicant: NantBio, Inc., Culver City, CA (US)

(72) Inventor: Kayvan Niazi, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 1290 days.

(21) Appl. No.: 16/767,497

(22) PCT Filed: Jan. 4, 2019

(86) PCT No.: PCT/US2019/012381
§ 371 (c)(1),
(2) Date: May 27, 2020

(87) PCT Pub. No.: WO2019/136273
PCT Pub. Date: Jul. 11, 2019

(65) Prior Publication Data
US 2020/0354679 A1    Nov. 12, 2020

Related U.S. Application Data

(60) Provisional application No. 62/614,298, filed on Jan. 5, 2018.

(51) Int. Cl.
| | | |
|---|---|---|
| *A61K 40/42* | (2025.01) | |
| *A61K 35/17* | (2015.01) | |
| *A61K 38/17* | (2006.01) | |
| *A61K 40/15* | (2025.01) | |
| *A61K 40/32* | (2025.01) | |
| *A61K 45/06* | (2006.01) | |
| *C07K 14/725* | (2006.01) | |
| *C12N 5/0783* | (2010.01) | |
| *C12N 15/62* | (2006.01) | |
| *A61K 48/00* | (2006.01) | |

(52) U.S. Cl.
CPC .......... *A61K 38/1774* (2013.01); *A61K 35/17* (2013.01); *A61K 40/15* (2025.01); *A61K 40/32* (2025.01); *A61K 40/428* (2025.01); *A61K 45/06* (2013.01); *C07K 14/7051* (2013.01); *C12N 5/0646* (2013.01); *C12N 15/62* (2013.01); *A61K 48/00* (2013.01); *C12N 2510/00* (2013.01)

(58) Field of Classification Search
None
See application file for complete search history.

(56) References Cited

U.S. PATENT DOCUMENTS

| | | |
|---|---|---|
| 2010/0261277 A1 | 10/2010 | Colton et al. |
| 2012/0059670 A1 | 3/2012 | Sanborn et al. |
| 2012/0066001 A1 | 3/2012 | Sanborn et al. |
| 2013/0287743 A1 | 10/2013 | Colton et al. |
| 2016/0083449 A1 | 3/2016 | Schmitt et al. |
| 2017/0281766 A1 | 10/2017 | Wiltzius |
| 2018/0044424 A1* | 2/2018 | June .................. A61K 39/4611 |

FOREIGN PATENT DOCUMENTS

| | | |
|---|---|---|
| DE | 11 2019 000 348 T5 | 9/2020 |
| JP | 2015223143 A | 12/2015 |
| WO | 2016126608 A1 | 8/2016 |
| WO | 2017027392 A1 | 2/2017 |
| WO | 2019/136273 A1 | 7/2019 |

OTHER PUBLICATIONS

Second Office Action received for German Patent Application Serial No. 112019000348.8 dated Jun. 8, 2021, 5 pages (Including English Translation).
International Preliminary Report on Patentability Chapter I received for PCT Application Serial No. PCT/US2019/012381 dated Jul. 16, 2020, 7 pages.
Office Action received for German Patent Application Serial No. 112019000348.8 dated Feb. 15, 2021, 7 pages (Including English Translation).
Bruhns et al., "Specificity and affinity of human Fcγ receptors and their polymorphic variants for human IgG subclasses", Blood, 2009, vol. 113, No. 16, pp. 3716-3725.
Hrvatin et al., "Differentiated human stem cells resemble fetal, not adult, β cells", Proceedings of the National Academy of Sciences, 2014, vol. 111, No. 8, pp. 3083-3043.
Dezell et al., "Natural killer cell differentiation from hematopoietic stem cells: a comparative analysis of heparin- and stromal cell-supported methods", Biology of Blood and Marrow Transplantation, 2012, vol. 18, pp. 536-545.
Carmen et al., "Concepts in antibody phage display", Briefings in Functional Genomics and Proteomics, 2002, vol. 1, No. 2, pp. 189-203.
Hosse et al., "A new generation of protein display scaffolds for molecular recognition", Protein Science, 2006, vol. 15, pp. 14-27.
Howell et al., "The HLA system: immunobiology, HLA typing, antibody screening and crossmatching techniques", Journal of Clinical Pathology, 2010, vol. 63, pp. 387-390.
Wherry E John, "T cell exhaustion", Nature Immunology, 2011, vol. 12, No. 6, pp. 492-499.
Pauken et al., "Overcoming T cell exhaustion in infection and cancer", Immunity and Cancer, Trends in Immunology, 2015, pp. 1-12.

(Continued)

*Primary Examiner* — Michael D Burkhart

(74) *Attorney, Agent, or Firm* — Umberg Zipser LLP; Martin Fessenmaier; Priti Phukan

(57) ABSTRACT

Compositions, methods and uses of genetically modified NK cells to treat a patient with a tumor are presented. The genetically modified NK cells express a protein complex having an α chain and a β chain T cell receptor, at least a portion of which is specific to a patient- or tumor-specific neoepitope, or a tumor associated antigen, and at least a portion of CD3δ, and at least a portion of CD3γ. The genetically modified NK cells can be administered to a cancer patient to induce, maintain or augment a T cell immune response against the cancer or the tumor.

5 Claims, No Drawings

(56) References Cited

OTHER PUBLICATIONS

D'Amour et al., "Production of pancreatic hormone-expressing endocrine cells from human embryonic stem cells", Nat Biotechnol., 2006, vol. 24, No. 11, 1 page.
Mahdi Batool Mutar, "A glow of HLA typing in organ transplantation", Clinical and Translational Medicine, 2013, vol. 2, No. 6, pp. 1-5.
Wessler et al., "The sound of tumor cell-microenvironmentcommunication—composed by the CancerCluster Salzburg research network", Cell Communication and Signaling, 2017, vol. 15, No. 20, 2 pages.
Grant Decision received for German Patent Application Serial No. 112019000348.8 dated Jul. 20, 2021, 14 pages (Including English Translation).
Birnbaum et al. "Molecular architecture of the $\alpha\beta$ T cell receptor-CD3 complex," Proceedings of the National Academy of Sciences USA, Dec. 9, 2014 (Dec. 9, 2014), vol. 111, No. 49, pp. 17576-17581. entire document.
International Search Report, International Application No. PCT/US2019/012381 dated: Jan. 4, 2019, pp. 1-9.

* cited by examiner

REPROGRAMMED T CELL-LIKE NK CELLS

This application claims priority to our US Provisional patent application with the Ser. No. 62/614,298, filed Jan. 5, 2018, which is incorporated in its entirety herein.

FIELD OF THE INVENTION

The field of the invention is immunotherapy making and using genetically modified immunocompetent cells having a T cell receptor or portion thereof for specifically targeting cancer cells.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Natural killer cells (also known as NK cells, K cells, and killer cells) are a type of lymphocyte and a component of the innate immune system. NK cells play a major role in the host-rejection of both tumors and virally infected cells. Typically, immune cells detect major histocompatibility complex (MHC) presented on infected cell surfaces, triggering cytokine release, causing lysis or apoptosis. NK cells are unique, however, as they have the ability to recognize stressed cells in the absence of antibodies and MHC, allowing for a much faster immune reaction. They were named "natural killers" because of the initial notion that they do not require activation to kill cells that are missing "self" markers of MHC class 1. This role is especially important because harmful cells that are missing MHC I markers cannot be detected and destroyed by other immune cells, such as T lymphocyte cells. NK cells contain cytotoxic; small granules in their cytoplasm contain special proteins such as perforin and proteases known as granzymes. Upon release in close proximity to a cell slated for killing, perforin forms pores in the cell membrane of the target cell through which the granzymes and associated molecules can enter, inducing apoptosis. The distinction between apoptosis and cell lysis is important in immunology-lysing a virus-infected cell would only release the virions, whereas apoptosis leads to destruction of the virus inside. NK cells are activated in response to interferons or macrophage-derived cytokines. They serve to contain infections while the adaptive immune response is generating antigen-specific cytotoxic T cells that can clear the infection.

T-cell receptor (TCR) is responsible for recognizing fragments of antigen as peptides bound to major histocompatibility complex (MHC) molecules. The binding between TCR and antigen peptides is of relatively low affinity and is degenerate, that is, many TCRs recognize the same antigen peptide and many antigen peptides are recognized by the same TCR.

TCR is a heterodimer that consists of an alpha ($\alpha$) chain and a beta ($\beta$) chain (encoded by TRA and TRB, respectively). In some T cells the TCR consists of gamma and delta ($\gamma/\delta$) chains (encoded by TRG and TRD, respectively). When the TCR engages with antigenic peptide and MHC (peptide/MHC), the T lymphocyte is activated through signal transduction, a series of biochemical events mediated by associated enzymes, co-receptors, specialized adaptor molecules, and activated or released transcription factors.

TCR is a disulfide-linked membrane-anchored heterodimeric protein normally consisting of the highly variable alpha ($\alpha$) and beta ($\beta$) chains expressed as part of a complex with the invariant CD3 chain molecules. T cells expressing this receptor are referred to as $\alpha:\beta$ (or $\alpha\beta$) T cells, though a minority of T cells express an alternate receptor, formed by variable gamma ($\gamma$) and delta ($\delta$) chains, referred as $\gamma\delta$ T cells. Each chain is composed of two extracellular domains: Variable (V) region and a Constant (C) region, both of Immunoglobulin superfamily (IgSF) domain forming antiparallel $\beta$-sheets. The constant region is proximal to the cell membrane, followed by a transmembrane region and a short cytoplasmic tail, while the variable region binds to the peptide/MHC complex. The variable domain of both the TCR $\alpha$-chain and $\beta$-chain includes three hypervariable or complementarity determining regions (CDRs). There is also an additional area of hypervariability on the $\beta$-chain (HV4) that does not normally contact antigen and, therefore, is not considered a CDR.

The residues in these variable domains are located in two regions of the TCR, at the interface of the $\alpha$- and $\beta$-chains and in the $\beta$-chain framework region that is thought to be in proximity to the CD3 signal-transduction complex. CDR3 is the main CDR responsible for recognizing processed antigen, although CDR1 of the alpha chain has also been shown to interact with the N-terminal part of the antigenic peptide, whereas CDR1 of the $\beta$-chain interacts with the C-terminal part of the peptide. CDR2 is thought to recognize the MHC. CDR4 of the $\beta$-chain is not thought to participate in antigen recognition, but has been shown to interact with superantigens.

Each recombined TCR possess unique antigen specificity, determined by the structure of the antigen-binding site formed by the $\alpha$ and $\beta$ chains in case of $\alpha\beta$ T cells or $\gamma$ and $\delta$ chains on case of $\gamma\delta$ T cells. The intersection of these specific regions (V and J for the alpha or gamma chain; V, D, and J for the beta or delta chain) corresponds to the CDR3 region that is important for peptide/MHC recognition. Since the cytoplasmic tail of the TCR is extremely short, making it unlikely to participate in signaling, these signaling molecules are vital in propagating the signal from the triggered TCR into the cell.

The human leukocyte antigen (HLA) system or complex is a gene complex encoding the major histocompatibility complex (MHC) proteins responsible for the regulation of the immune system in humans. HLAs corresponding to MHC class I (A, B, and C) present peptides from inside the cell. Foreign antigens presented by MHC class I attract killer T-cells (CD8 positive- or cytotoxic T-cells) that destroy cells. MHC class I proteins associate with $\beta$2-microglobulin, which unlike the HLA proteins is encoded by a gene on chromosome 15. HLAs corresponding to MHC class II (DP, DM, DOA, DOB, DQ, and DR) present antigens from outside of the cell to T-lymphocytes. These particular antigens stimulate the multiplication of T-helper cells, which in turn stimulate antibody-producing B-cells to produce antibodies to that specific antigen. Self-antigens are suppressed by regulatory T cells. HLAs corresponding to MHC class III encode components of the complement system.

More recently, genetically engineered receptors, chimeric antigen receptors (CARs), have been developed by grafting antigen specific binding portions onto signaling portions to so drive immune cells carrying the CAR to the targeted cells (e.g., infected cells, cancer cells, etc.). Notably, however, such approach has traditionally been used to genetically modify T cells to specifically elicit T cell response to a molecule that the expressed CAR recognizes (e.g., CAR-T cells). Thus, even though genetic modification of T cells with recombinant CAR molecule is known in the art, it is largely unexplored how other immune cells can be transformed by expressing CAR or recombinant T cell receptor, and how such genetically modified non-T cells can be used in immune therapy.

SUMMARY OF THE INVENTION

T cell receptors recognizing particular antigens or neoepitopes on certain tumor or cancer cells may over time become exhausted. It would be desirable to provide genetically modified immunocompetent cells to recognize particular antigens or neoepitopes on these tumor or cancer cells. The inventive subject matter is directed to various compositions of, methods for making, and use of immunocompetent cells such as NK cells genetically modified to express a T cell receptor complex or portion thereof to induce, maintain or augment a cellular immune response. Thus, one aspect of the subject matter includes a genetically engineered immunocompetent cell such as a NK cell including a recombinant nucleic acid encoding a T cell receptor complex or portion thereof. The T cell receptor complex preferably includes an extracellular portion that specifically binds a tumor (neo)epitope, a tumor associated antigen, or a self-lipid, an intracellular activation domain, and a transmembrane linker coupling the extracellular fragment to the intracellular activation domain.

In one aspect of the inventive subject matter, the inventors contemplate a genetically modified immunocompetent cell such as an NK cell expressing a recombinant protein complex. The protein complex includes an α chain T cell receptor, a β chain T cell receptor, at least a portion of CD3δ, and at least a portion of CD3γ. At least a portion of the α chain T cell receptor and/or the β chain T cell receptor is specific to a patient-specific, tumor-specific neoepitope, or tumor associated antigen, or self-lipid. Preferably, a portion of the protein complex is encoded by a first nucleic acid segment encoding an α chain T cell receptor and a β chain T cell receptor, in which the portions encoding α and β chain receptor are separated by a first self-cleaving 2A peptide sequence. Also, another portion of the protein complex may be encoded by a second nucleic acid segment encoding at least a portion of CD3δ and at least a portion of CD3γ, in which the portions encoding at least a portion of CD3δ and the at least portion of CD3γ are separated by a second self-cleaving 2A peptide sequence. In this embodiment, it is also preferred that the first nucleic acid segment and the second nucleic acid segment are separated by a third self-cleaving 2A peptide sequence. Optionally, the T cell receptor may further include one or more ITAM motifs in the intracellular signaling portions such as, for instance, CD3ζ and/or DAP10, DAP12, or one or more chimeric proteins between CD3ζ and/or DAP10, DAP12, and hence include nucleic acid segments encoding the same that may likewise be separated by one or more self-cleaving 2A peptide sequences.

In another aspect of the inventive subject matter, the inventors contemplate a method of making a genetically modified immunocompetent cell such as an NK cell expressing a recombinant protein complex. The protein complex includes α chain T cell receptor, β chain T cell receptor, at least a portion of CD3δ, and at least a portion of CD3γ. At least a portion of the α chain T cell receptor and/or the β chain T cell receptor is specific to a patient-specific, tumor-specific neoepitope, or tumor associated antigen, or self-lipid. The method features introducing a nucleic acid segment encoding an α chain T cell receptor and a β chain T cell receptor into the immunocompetent cell such as an NK cell, in which the portions encoding α and β chain T cell receptor are separated by a first self-cleaving 2A peptide sequence. Also, the method may feature introducing a second nucleic acid segment encoding at least a portion of CD3δ and at least a portion of CD3γ into the cell, in which the portions encoding at least a portion of CD3δ and the at least portion of CD3γ are separated by a second self-cleaving 2A peptide sequence. It is also preferred that the first nucleic acid segment and the second nucleic acid segment are separated by a third self-cleaving 2A peptide sequence. Optionally, the method may further feature introducing one or more nucleic acid segments expressing one or more ITAM motifs in the intracellular signaling portions such as, for instance, CD3ζ and/or DAP10, DAP12, or one or more chimeric proteins between CD3ζ and/or DAP10, DAP12. These nucleic acid segments may likewise be separated by one or more self-cleaving 2A peptide sequences.

In still another aspect of the inventive subject matter, the inventors contemplate a method of treating a patient having a cancer or a tumor featuring providing a genetically modified immunocompetent cell such as an NK cell expressing a recombinant protein complex to the patient. The protein complex includes an α chain T cell receptor, a β chain T cell receptor, at least a portion of CD3δ, and at least a portion of CD3γ. At least a portion of the α chain T cell receptor and/or the β chain T cell receptor is specific to a patient-specific, tumor-specific neoepitope, or tumor associated antigen, or self-lipid. The genetically modified immunocompetent cell such as an NK cell contains a nucleic acid segment encoding an α chain T cell receptor and a β chain T cell receptor in which the portions encoding α and β chain T cell receptor are separated by a first self-cleaving 2A peptide sequence. Also, the genetically modified immunocompetent cell such as a NK cell may contain a second nucleic acid segment encoding at least a portion of CD3δ and at least a portion of CD3γ into the cell, in which the portions encoding at least a portion of CD3δ and the at least portion of CD3γ are separated by a second self-cleaving 2A peptide sequence. In this embodiment, it is also preferred that the first nucleic acid segment and the second nucleic acid segment are separated by a third self-cleaving 2A peptide sequence. The method further features administering the genetically modified immunocompetent cells such as NK cells to the patient in a dose and a schedule effective to induce, maintain or augment an immune response against the tumor or cancer. The T cell receptor complex may be naturally occurring in the patient or from a donor. The T cell receptor complex from a donor may be selected to be of any desired HLA compatibility with respect to the patient.

In still another aspect of the inventive subject matter, the inventors contemplate a method of a maintaining, inducing or supplementing a T cell immune response in a patient having a cancer or a tumor. A genetically modified immunocompetent cell such as an NK cell expressing a recombinant protein complex or a plurality of the genetically modified immunocompetent cells such as NK cells are provided to the patient. The protein complex includes an α chain T cell receptor, a β chain T cell receptor, at least a portion of CD3δ, and at least a portion of CD3γ. At least a portion of the α chain T cell receptor and/or the β chain T cell receptor is specific to a patient-specific, tumor-specific neoepitope, or tumor associated antigen, or self-lipid. Preferably, a portion of the protein complex is encoded by a first nucleic acid segment encoding an α chain T cell receptor and a β chain T cell receptor, in which the portions encoding α and β chain receptor are separated by a first self-cleaving 2A peptide sequence. Also, another portion of the protein complex may be encoded by a second nucleic acid segment encoding at least a portion of CD3δ and at least a portion of CD3γ, in which the portions encoding at least a portion of CD3δ and the at least portion of CD3γ are separated by a second self-cleaving 2A peptide sequence. It is also preferred that the first nucleic acid segment and the second nucleic acid segment are separated by a third self-cleaving 2A peptide sequence. The method further features administering the genetically modified immunocompetent cells such as NK cells to the patient in a dose and a schedule effective to induce, maintain or augment a cellular immune response against the cancer or tumor. The T cell receptor complex may be naturally occurring in the patient or from a donor. The T cell receptor complex from the donor may be selected to be of any desired HLA compatibility with respect to the patient.

In still another aspect of the inventive subject matter, the inventors contemplate a method of maintaining, augmenting or inducing a T cell immune response in a patient having a tumor or cancer is provided. A plurality of immunocompetent cells such as NK cells of a patient or a donor is obtained from the patient's or the donor's bodily fluid. The cells are genetically modified to express a protein complex including at least an α chain T cell receptor, a β chain T cell receptor, at least a portion of CD3δ, and at least a portion of CD3γ. Optionally, the cells may be modified to express one or more ITAM motifs in the intracellular signaling portions such as, for instance, CD3ζ and/or DAP10, DAP12, or one or more chimeric proteins between CD3ζ and/or DAP10, DAP12. The method further continues with administering the genetically modified immunocompetent cells such as NK cells to the patient in a dose and a schedule effective to induce an immune response against the tumor. The T cell receptor complex may be naturally occurring in the patient or from a donor. The T cell receptor complex from the donor may be selected to be of any desired HLA compatibility with respect to the patient.

In still another aspect of the inventive subject matter, the inventors contemplate a pharmaceutical composition containing a plurality of genetically modified immunocompetent cells such as NK cells expressing a recombinant protein complex. The protein complex includes an α chain T cell receptor, a β chain T cell receptor, at least a portion of CD3δ, and at least a portion of CD3γ.

At least a portion of the α chain T cell receptor and/or the β chain T cell receptor is specific to a patient-specific, tumor-specific neoepitope, or tumor associated antigen, or self-lipid. Preferably, a portion of the protein complex is encoded by a first nucleic acid segment encoding an α chain T cell receptor and a β chain T cell receptor, in which the portions encoding α and β chain receptor are separated by a first self-cleaving 2A peptide sequence. Also, another portion of the protein complex may be encoded by a second nucleic acid segment encoding at least a portion of CD3δ and at least a portion of CD3γ, in which the portions encoding at least a portion of CD3δ and the at least portion of CD3γ are separated by a second self-cleaving 2A peptide sequence. It is also preferred that the first nucleic acid segment and the second nucleic acid segment are separated by a third self-cleaving 2A peptide sequence. Optionally, the T cell receptor protein complex may further include one or more ITAM motifs in the intracellular signaling portions such as, for instance, CD3ζ and/or DAP10, DAP12, or one or more chimeric proteins between CD3ζ and/or DAP10, DAP12, and hence include nucleic acid segments encoding the same that may likewise be separated by one or more self-cleaving 2A peptide sequences.

NK cells express the surface markers CD16 (FcγRIII) and CD56. They may be identified by an antibody against a portion of CD16 (FcγRIII) or CD56. The genetically modified immunocompetent cells may be enriched using a binding molecule specific to the plurality of the cells. The population of enriched cells may be expanded ex vivo, preferably in the presence of one or more cytokines. Then, the expanded immunocompetent cells such as NK cells may be administered to the patient in a dose and a schedule effective to induce, maintain, or augment a cell immune response against the tumor.

In still another aspect of the inventive subject matter, the inventors contemplate a genetically engineered natural killer cell that includes a recombinant nucleic acid encoding a protein complex having an α chain T cell receptor, a β chain T cell receptor, at least a portion of CD3δ, and at least a portion of CD3γ. It is mostly preferred that at least a portion of the α chain T cell receptor or a β chain T cell receptor is specific to a patient- or tumor-specific neoepitope, or a tumor associated antigen.

Preferably, the recombinant nucleic acid comprises a first nucleic acid segment encoding an α chain T cell receptor and a β chain T cell receptor, the α and β chain receptor being separated by a first self-cleaving 2A peptide sequence, and a second nucleic acid segment encoding at least a portion of CD3δ and at least a portion of CD3γ, the at least a portion of CD3δ and the at least a portion of CD3γ being separated by a second self-cleaving 2A peptide sequence. In some embodiments, the first nucleic acid segment and the second nucleic acid segment are separated by a third self-cleaving 2A peptide sequence. In some embodiments, the portion of CD3γ or CD3δ comprises an immunoreceptor tyrosine-based activation motif (ITAM). Also preferably, the natural killer cell is generated from a NK-92 derivative cell.

In still another aspect of the inventive subject matter, the inventors contemplate a pharmaceutical composition for treating a patient having a tumor or a cancer, where the pharmaceutical composition comprises a plurality of the genetically engineered natural killer cells as described above.

In still another aspect of the inventive subject matter, the inventors contemplate a method of inducing an NK cell immune response against a tumor in a patient having the tumor. This method includes a step of providing a genetically modified NK cell expressing a recombinant protein comprising having an α chain T cell receptor, a β chain T cell receptor, at least a portion of CD3δ, and at least a portion of CD3γ, wherein at least a portion of the α chain T cell receptor or a β chain T cell receptor is specific to a patient- or tumor-specific neoepitope, or a tumor associated antigen, and a step of administering to the patient a genetically modified NK cell to the patient in a dose and a schedule effective to treat the tumor. It is contemplated that the dose and the schedule is effective to induce, maintain or augment an immune response against the tumor.

Preferably, the portion of CD3γ or CD3δ comprises an immunoreceptor tyrosine-based activation motif (ITAM). Also preferably, the natural killer cell the natural killer cell is generated from a NK-92 derivative cell.

Most typically, the genetically modified NK cell includes a recombinant nucleic acid comprising a first nucleic acid segment encoding an α chain T cell receptor and a β chain T cell receptor, the α and β chain receptor being separated by a first self-cleaving 2A peptide sequence, and a second nucleic acid segment encoding at least a portion of CD3δ and at least a portion of CD3γ, the at least a portion of CD3δ and the at least a portion of CD3γ being separated by a second self-cleaving 2A peptide sequence. In some embodiments, the first nucleic acid segment and the second nucleic acid segment are separated by a third self-cleaving 2A peptide sequence. In some embodiments, at least one of the first and second nucleic acid segments T cell receptor are homologous to an autologous T cell receptor of the patient.

In some embodiments, the method may further comprise a step of providing a condition to the tumor to express a CD1d on a surface of the tumor. In some embodiments, the condition may include introducing a nucleic acid composition comprising a first nucleic acid segment encoding a CD1d. In such embodiments, the nucleic acid composition may further comprise a second nucleic acid segment encoding p99. In other embodiments, the condition comprises a stress condition to the tumor and/or a condition of administering an inhibitor of HDAC to increase CD1d expression in the tumor.

In still another aspect of the inventive subject matter, the inventors contemplate a use of a genetically modified natural killer cell and/or a pharmaceutical composition as described above for treating a patient having a tumor.

Various objects, features, aspects and advantages of the inventive subject matter will become more apparent from the following detailed description of preferred embodiments.

DETAILED DESCRIPTION

The inventors have now discovered that immunocompetent cells such as NK cells may be genetically modified to express a T cell receptor or a portion thereof that specifically binds to a tumor specific or tumor associated antigen, a neoepitope, and/or a self-lipid of the tumor, which consequently triggers a cellular immune response against the tumor.

As used herein, the term "tumor" refers to, and is interchangeably used with one or more cancer cells, cancer tissues, malignant tumor cells, or malignant tumor tissue, that can be placed or found in one or more anatomical locations in a human body. As used herein, the term "bind" refers to, and can be interchangeably used with a term "recognize" and/or "detect", an interaction between two molecules with a high affinity with a $K_D$ of equal or less than $10^{-6}$M, or equal or less than $10^{-7}$M. As used herein, the term "provide" or "providing" refers to and includes any acts of manufacturing, generating, placing, enabling to use, or making ready to use.

As used herein, the term "maintaining or augmenting a T cell response" means increasing the number of activated cells expressing a T cell receptor present to provide a cellular immune response to a tumor or cancer cell expressing a particular tumor or cancer neoepitope, antigen or self-lipid. As used herein, the term "inducing a T cell response" means providing a group of activated cells present to provide a cellular immune response to a tumor or cancer cell binding to a T cell receptor in the absence of a population of T cells present in the patient effective to provide a cellular immune response to a particular tumor or cancer neoepitope, antigen or self-lipid. As used herein, the term "immunocompetent cells" includes all cells of the immune system including all lymphocytes, and including but not limited to T cells, B cells, dendritic cells, macrophages, NKT cells and the like.

NK Cells

With respect to suitable NK cells it is generally contemplated that the NK cells may be an autologous NK cell from a subject that will receive genetically modified NK cells. Such autologous NK cells may be isolated from whole blood, or cultivated from precursor or stem cells using methods well known in the art. Moreover, it should also be appreciated that the NK cells need not be autologous, but may be allogenic, or heterologous NK cells. However, in particularly preferred aspects of the inventive subject matter, the NK cells are genetically engineered to achieve one or more desirable traits, are NK92 cells or derivatives of NK92 cells. Additionally, suitable NK cells will also be continuously growing ('immortalized') cells. For example, in one particularly preferred aspect of the inventive subject matter, the genetically engineered NK cell is a NK92 derivative that is modified to have reduced or abolished expression of at least one killer cell immunoglobulin-like receptor (KIR), which will render such cells constitutively activated (via lack of or reduced inhibition).

NK92 cells exhibit an unusual receptor expression profile, expressing a relatively large number of activating (e.g., NKp30, NKp46, 2B4, NKGD, E, CD28) receptors. Conversely, NK92 cells also expresses few inhibitory receptors (e.g., NKGA/B, low levels of KIR2DL4, ILT-2), and lack most of the killer inhibitory receptors (KIRs) clonally expressed on normal NK cells. In addition, NK92 expresses relatively high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. Moreover, NK92 cells also express other molecules implicated immune effector cell regulation (CD80, CD86, CD40L, TRANCE) whose relevance in NK killing is unclear.

Moreover, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells ('activated natural killer cells).

The genetically engineered NK cell may also be an NK92 derivative that is modified to express the high-affinity Fcγ receptor (CD16). Sequences for high-affinity variants of the Fcγ receptor are well known in the art (see e.g., Blood 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells ('high-affinity natural killer cells). Such cells may then be further modified to express one or more ligands for one or more inhibitory receptors of the NK cells of the host organism.

The genetically engineered NK cell may be genetically engineered to express a chimeric T-cell receptor. In especially preferred aspects, the chimeric T-cell receptor will have a scFv portion or other ectodomain with binding specificity against a tumor associated antigen, a tumor specific antigen, and a cancer neoepitope. As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells'). Such cells may then be further modified to express one or more ligands for one or more inhibitory receptors of the NK cells of the host organism. The inventors contemplates that use of haNK cells or taNK cells may provide dual-specificity of the genetically modified cytotoxic cells as described later to target any cancer cells or autoimmunity-affected cells by recognizing the cancer- or autoimmune-specific epitope and concurrently recognizing the lipid antigen presented on those cell surfaces.

In some instances, the NK cells may be provided using methods for directing stem cell differentiation. As used herein, the phrase "directing stem cell differentiation" and "directed differentiation" has its ordinary meaning in the art and may refer to a differentiation process that is non-spontaneous and is controllably induced by one or more features of articles or methods used for differentiation. A method for directed differentiation may comprise directing the differentiation of stem cells to a particular lineage on the articles, described herein. The cell differentiation method may include directing the differentiation of stem cells on an oxygen permeable substrate having at least a portion of a surface coated with a matrix (e.g., formed via an iCVD process), at least a portion of which is covalently bound to biological molecules, such as proteins. The directed differentiation features exposing the stem cells to certain soluble factors and/or controlling or altering the $pO_2$ of the cell during the differentiation process. Non-limiting examples of directed differentiation methods comprising controlling oxygen are described in U.S. Publication No. 2013/0287743 filed Apr. 29, 2013 and U.S. Publication No. 2010/0261277 filed Jun. 13, 2008, entitled "Methods and Compositions for Enhanced Differentiation from Embryonic Stem Cells"; D'Amour et al. *Nat. Biotechnol.* 24, 1393-1401 (2006); and Hrvatin, et al., "Differentiated human stem cells resemble fetal, not adult, β-cells" *PNAS* 2014, and are incorporated herein by reference in their entirety. Further methods are described in *Biol Blood Marrow Transplant.* 2012 April; 18(4):536-45; Dezell et al., "Natural killer cell differentiation from hematopoietic stem cells: a comparative analysis of heparin- and stromal cell-supported methods," *Biology of Blood and Marrow Transplantation*, April 2012; 18(4):536-545; Nil et al., "Human Pluripotent Stem Cells Produce Natural Killer Cells That Mediate Anti-HIV-1 Activity by Utilizing Diverse Cellular Mechanisms," *Journal of Virology*, the disclosures of which are herein incorporated by reference.

Where the patient's autologous NK cells are preferred, NK cells of a patient can be obtained, isolated and then expanded to be reintroduced to the patient. NK cells can be obtained from any suitable tissues of a patient, so long as NK cells are present in the tissue. NK cells express the surface markers CD16 (FcγRIII) and CD56 and may be identified using an antibody specific to a portion of these or other cell markers. Most typically, suitable tissue sources include whole blood. It is contemplated that the number of NK cells expected to be present in the tissue may vary among individuals (e.g., based on age, gender, health status, ethnicity, etc.) and the type of tissue (e.g., whole blood, cerebrospinal fluid, etc.). For example, in order to obtain NK cells from a patient having a tumor, at least 2 ml, preferably at least 5 ml, more preferably at least 10 ml of whole blood can be obtained from the patient.

While adult's peripheral blood is the most accessible source to obtain NK cells, it is also contemplated that the patient's NK can be obtained from the patient's stored umbilical cord blood. While it may vary depending on the storage conditions, in order to obtain NK cells from a patient's umbilical cord blood, at least 0.5 ml, preferably at least 1 ml, more preferably at least 2 ml of umbilical cord blood can be obtained from the patient.

From the bodily fluid of the patient, which includes many different types of cells (e.g., erythrocytes, platelets, neutrophils, lymphocytes, etc.), NK cells can be isolated using several known molecular markers or their binding molecules, for instance, CD16 (FcγRIII) and CD56. For example, an antibody against a NK cell surface antigen can be immobilized on a bead (e.g., agarose beads, biotin-coated beads, etc.), and then contacted with the patient's bodily fluid. In some embodiments, the inventors contemplate that the enriching process can be performed with two or more binding molecules to increase specificity, preferably in two separate and sequential contacting processes.

In a preferred embodiment, the NK cells bound to the antibodies can be eluted in a smaller volume of liquid (e.g., cell culture media, etc.) than the original sample volume (e.g., blood volume, etc.) so that the NK cells can be enriched after the isolation (e.g., NK cells in 10 ml volume of blood can be isolated in 0.5 ml volume of cell culture media, resulting in about 20 times enrichment of NKT cells after isolation, etc.). In some embodiments, where NK cells are isolated via two or more contacting processes, the NK cells can be further enriched by further reducing the volume of elution media (e.g., cell culture media, etc.) in the second contacting process (e.g., 10 ml original sample volume can be reduced to 2 ml eluted cells in the first contacting process, and then further reduced to 0.5 ml eluted cells in the second contacting process, etc.). It is especially preferred that the NK cells are enriched at least 5 times, preferably at least 10 times, more preferably at least 20 times compared to the number of cells/volume of original bodily fluid sample.

In other embodiments, the NK cells can be isolated from other cells in the patient's bodily fluid using flow cytometry (e.g., fluorescence activated cell sorting (FACS), etc.) or magnetic activated cell sorting (MACS). For example, NK cells can be isolated from other cells using fluorescence tagged or magnetic-particle tagged antibody. The inventors also contemplate that the isolated cells by flow cytometry or MACS can be further enriched using a pull-down assay with beads coated with peptide antigen.

Additionally, the population of isolated and enriched NK cells can be further increased via ex vivo expansion of the NK cells. The ex vivo expansion of NK cells can be performed in any suitable method with any suitable materials that can expand NK cells at least 10 times, preferably at least 100 times in 7-21 days. For example, isolated and enriched NK cells can be placed in a cell culture media (e.g., AIMV® medium, RPMI1640® etc.) that includes one or more conditions that may include addition of any molecules that can stimulate NK growth, induce cell division of NK, and/or stimulate cytokine release from NK that can further expand NK cells. Thus the activating molecules include one or more cytokines (e.g., IL-2, IL-5, IL-7, IL-8, IL-12, IL-12, IL-15, IL-18, and IL-21, preferably human recombinant IL-2, IL-5, IL-7, IL-8, IL-12, IL-12, IL-15, IL-18, and IL-21, etc.) in any desirable concentration (e.g., at least 10 U/ml, at least 50 U/ml, at least 100 U/ml), T cell receptor antibodies on the surface of genetically modified NK cells (e.g., anti-CD2, anti-CD3, anti-CD28,α-TCR-Vα24+ antibodies, preferably immobilized on beads, etc.), a glycolipid (e.g., α-Glc-Cer, β-ManCer, GD3, etc.), a glycolipid coupled with CD1 (e.g., CD1d, etc.), etc.

With respect to these activating conditions, it is contemplated that the dose and schedule of providing activating conditions may vary depending on the initial number of genetically modified NK cells and the condition of the genetically modified NK cells. In some embodiments, a single dose of cytokine (e.g., 100 U/ml) can be employed for at least 3 days, at least 5 days, at least 7 days, at least 14 days, at least 21 days. In other embodiments, the dose of cytokine may be increased or decreased during the expansion period (e.g., 200 U/ml for first 3 days and 100 U/ml for next 14 days, or 100 U/ml for first 3 days and 200 U/ml for next 14 days, etc.). Also it is contemplated that different types of cytokines can be used in combination or separately during the ex vivo expansion (e.g., IL-15 for first 3 days and IL-18 for next 3 days, or combination of IL-15 and IL-18 for 14 days, etc.).

Optionally, the expanded genetically modified NK cells can be further activated under conditions that will increase cytotoxicity. The condition to increases cytotoxicity include contacting the expanded genetically modified NK cells with T cell receptor antibodies (e.g., anti-CD2, anti-CD3, anti-CD28, α-TCR-Vα24+ antibodies, preferably immobilized on beads, etc.), a glycolipid (e.g., α-GlcCer, β-ManCer, GD3, etc.), or a glycolipid coupled with CD1 (e.g., CD1d, etc.), for a desired period (e.g., at least 1 hour, at least 6 hours, at least 24 hours, at least 3 days, at least 7 days, etc.). The cytotoxicity of the expanded and activated NK cells can be determined by measuring the amount of cytokine release (e.g., IL-2, IL-13, IL-17, IL-21, TNF-α, etc.) from the NK cells.

NK cell expressing a recombinant T cell receptor complex: The inventors contemplate that NK cells can be genetically modified by introducing a recombinant nucleic acid composition encoding a protein complex to the NK cells. Most typically, the protein complex includes at least one or more distinct peptides having an extracellular domain of a T cell receptor, and at least one or more distinct peptides of the intracellular domain of a T cell receptor. For example, one preferred protein complex includes an α chain of a T cell receptor, a β chain of a T cell receptor, at least a portion of CD3δ (preferably cytoplasmic domain), and at least a portion of CD3γ (preferably cytoplasmic domain). In another example, the protein complex may include a γ chain T cell receptor and a δ chain T cell receptor instead of the α and β chains of T cell receptors. Additionally, the protein complex may include in one or more instances, at least a portion of a CD3ξ and at least a portion of a CD3ζ.

While any suitable forms of recombinant nucleic acid composition to encode the protein complex can be used, the inventors contemplate that the protein complex can be encoded by a single nucleic acid comprising a plurality of segments, each of which encodes a distinct peptide. Thus, in one preferred embodiment, the nucleic acid composition includes a first nucleic acid segment encoding two distinct peptides: an α chain T cell receptor and a β chain T cell receptor (or alternatively, γ chain T cell receptor and δ chain T cell receptor), and a second nucleic acid segment encoding two peptides, namely at least a portion of one type of T-cell receptor (e.g., CD3δ) and at least a portion of another type of T-cell receptor (e.g., CD3γ), or alternatively, encoding one or more ζ-chain substituting for the portion of CD3δ or the portion of CD3γ. It is contemplated that each distinct peptide encoded by the first and second nucleic acid segments is a full length protein (e.g., full length alpha and β chain T cell receptor and co-receptors). Yet, it is also contemplated that at least one or more distinct peptides encoded by the first and second nucleic acid segments can be a truncated or a portion of the full length proteins.

Preferably, the first and second nucleic acid segments are mRNAs, each of which comprises two sub-segments of mRNA, which encode a T cell receptor (e.g., sub-segment A is an mRNA of α chain T cell receptor and sub-segment B is an mRNA of β chain T cell receptor, etc.), followed by poly A tail. It is further preferred that the two sub-segments of mRNA are separated by nucleic acid sequences encoding a type of 2A self-cleaving peptide (2A). As used herein, 2A self-cleaving peptide (2A) refers to any peptide sequences that can provide a translational effect known as "stop-go" or "stop-carry" such that two sub-segments in the same mRNA fragments can be translated into two separate and distinct peptides. Any suitable types of 2A peptide sequences are contemplated, including porcine teschovirus-1 2A (P2A), thosea asigna virus 2A (T2A), equine rhinitis A virus 2A (E2A), foot and mouth disease virus 2A (F2A), cytoplasmic polyhedrosis virus (BmCPV 2A), and flacherie virus (BmIFV 2A). In some embodiments, same type of 2A sequence can be used between two sub-segments of both first and second nucleic acid segments (e.g., fist nucleic acid segment: mRNA of α chain receptor-T2A-mRNA of β chain receptor; second nucleic acid segment: mRNA of α chain receptor-T2A-mRNA of β chain receptor). In other embodiments, different types of 2A sequence can be used between two sub-segments of both first and second nucleic acid segments (e.g., fist nucleic acid segment: mRNA of α chain receptor-T2A-mRNA of β chain receptor; second nucleic acid segment: mRNA of α chain receptor-P2A-mRNA of β chain receptor).

Additionally, the inventors contemplate that the first and second nucleic acid segments can also be present in a single nucleic acid (mRNA), for example, connected by a 2A sequence. In this embodiment, the sub-segments of first and second nucleic acid segments can be arranged in any suitable order (e.g., α chain-β chain-CD3γ-CD3δ, β chain-CD3γ-α chain-CD3δ, etc.), with any suitable combination of the same or different 2A sequences (e.g., α chain-T2A-β chain-P2A-CD3γ-F2A- CD3δ, β chain- P2A-CD3γ-T2A-α chain-F2A-CD3δ, etc.), followed by poly A tail at the 3' of the single mRNA.

With respect to the mRNA sequence of the first and second nucleic acid segments, it is preferred that the mRNA sequences are selected based on the sequence of the tumor neoepitope, tumor associated antigen, or self-lipid that the T cell receptor protein complex targets to. The T cell receptors may be selected from those encoding sequences drawn from exhausted T cells of a patient. For example, it is preferred that the peptide encoded by the first nucleic acid segment has an actual or predicted affinity to the tumor epitope at least with a $K_D$ of at least equal or less than $10^{-6}M$, preferably at least equal or less than $10^{-7}M$, more preferably at least equal or less than $10^{-8}M$. Any suitable methods to identify the first nucleic acid segment sequence that has high binding affinity to the tumor epitope are contemplated. For example, a nucleic acid sequence of first nucleic acid segment can be identified via a mass screening of peptides having various affinities to the tumor epitope via any suitable in vitro assays (e.g., flow cytometry, SPR assay, a kinetic exclusion assay, etc.), or by mRNA display technique (e.g., RNA bind-n-seq, etc.).

The recombinant nucleic acid also includes a second nucleic acid segment (a sequence element) encoding an intracellular activation domain of the recombinant protein. Most typically, the intracellular activation domain includes one or more ITAM activation motifs (immunoreceptor tyrosine-based activation motif, YxxL/I-$X_{6-8}$-YXXL/I), which triggers signaling cascades in the cells expressing the motifs. Any suitable nucleic acid sequences including one or more ITAM activation motifs are contemplated. For example, the sequence of the activation domain can be derived from a cytotoxic cell receptor (e.g., NK cell receptor, NKT cell receptor, etc.) including one or more ITAM activation motif (e.g., intracellular tail domain of killer activation receptors (KARs), NKp30, NKp44, and NKp46, etc.). In another example, the sequence of the activation domain can be derived from a tail portion of a T-cell antigen receptor (e.g., CD3ζ, CD28, etc.). In some embodiments, the nucleic acid sequence of the intracellular activation domain can be modified to add/remove one or more ITAM activation motif to modulate the cytotoxicity of the cells expressing the recombinant protein.

The first and second nucleic acid segments are optionally connected via a third nucleic acid segment encoding a linker portion of the recombinant protein. Preferably, the linker portion of the recombinant protein includes at least one transmembrane domain. Additionally, the inventors contemplate that the linker portion of the recombinant protein further includes a short peptide fragment (e.g., spacer with a size of between 1-5 amino acids, or between 3-10 amino acids, or between 8-20 amino acids, or between 10-22 amino acids) between the transmembrane domain and the extracellular single-chain variant fragment, and/or another short peptide fragment between the transmembrane domain and the intracellular activation domain. In some embodiments, the nucleic acid sequence of transmembrane domain and/or one or two short peptide fragment(s) can be derived from the same or different molecule from which the sequence of intracellular activation domain is obtained.

For example, where the intracellular activation domain is a portion of CD3ζ, the entire third nucleic acid segment (encoding both transmembrane domain and short peptide fragment) can be derived from CD3ζ (same molecule) or CD28 (different molecule). In other embodiments, the third nucleic acid segment is a hybrid sequence, in which at least a portion of the segment is derived from a different molecule than the rest of the segment. In a further example, where the intracellular activation domain is a portion of CD3ζ, the sequence of the transmembrane domain can be derived from CD3ζ and a short fragment connecting the transmembrane domain, and the extracellular single-chain variant fragment may be derived from CD28 or CD8.

In still other contemplated embodiments, the recombinant nucleic acid includes a nucleic acid segment encoding a signaling peptide that directs the recombinant protein to the cell surface. Any suitable and/or known signaling peptides are contemplated (e.g., leucine rich motif, etc.). Preferably, the nucleic acid segment encoding an extracellular single-chain variant fragment is located in the upstream of the first nucleic acid segment encoding an extracellular single-chain variant fragment such that the signal sequence can be located in N-terminus of the recombinant protein. However, it is also contemplated that the signaling peptide can be located in the C' terminus of the recombinant protein, or in the middle of the recombinant protein.

In some embodiments, the recombinant nucleic acid also includes a sequence element that controls expression of the recombinant protein, and all manners of control are deemed suitable for use herein. For example, where the recombinant nucleic acid is an RNA, expression control may be exerted by suitable translation initiation sites (e.g., suitable cap structure, initiation factor binding sites, internal ribosome entry sites, etc.) and a polyA tail (e.g., where length controls stability and/or turnover), while recombinant DNA expression may be controlled via a constitutively active promoter, a tissue specific promoter, or an inducible promoter.

With respect to recognized antigens it should be noted that all antigens that bind to MHC class I are deemed suitable for use herein. Consequently, contemplated antigens especially include one or more tumor associated antigens, self-lipids, and especially tumor neoepitopes. Most typically, the tumor associated antigens and neoepitopes (which are typically patient-specific and tumor-specific) can be identified from the omics data obtained from the cancer tissue of the patient or normal tissue (of the patient or a healthy individual), respectively. Omics data typically includes information related to genomics, transcriptomics, proteomics. As used herein, the cancer cells or normal cells (or tissues) may include cells from a single or multiple different tissues or anatomical regions, cells from a single or multiple different hosts, as well as any permutation of combinations.

Omics data of cancer and/or normal cells preferably comprise a genomic data set that includes genomic sequence information. Most typically, the genomic sequence information comprises DNA sequence information that is obtained from the patient (e.g., via tumor biopsy), most preferably from the cancer tissue (diseased tissue) and matched healthy tissue of the patient or a healthy individual. For example, the DNA sequence information can be obtained from a pancreatic cancer cell in the patient's pancreas (and/or nearby areas for metastasized cells), and a normal pancreatic cells (non-cancerous cells) of the patient or a normal pancreatic cells from a healthy individual other than the patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAM format, SAM format, FASTQ format, or FASTA format. However, it is especially preferred that the data sets are provided in BAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

Likewise, computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Such analysis advantageously reduces false positive neoepitopes and significantly reduces demands on memory and computational resources.

The so obtained neoepitopes may then be subject to further detailed analysis and filtering using predefined structural and expression parameters, and sub-cellular location parameters. For example, it should be appreciated that neoepitope sequences are only retained provided they will meet a predefined expression threshold (e.g., at least 20%, 30%, 40%, 50%, or higher expression as compared to normal) and are identified as having a membrane associated location (e.g., are located at the outside of a cell membrane of a cell). Further contemplated analyses will include structural calculations that delineate whether or not a neoepitope or a tumor associated antigen, or a self-lipid is likely to be solvent exposed, presents a structurally stable epitope, etc.

Consequently, it should be recognized that epitopes can be identified in an exclusively in silico environment that ultimately predicts potential epitopes that are unique to the patient and tumor type. So identified epitope sequences are then synthesized in vitro to generate the corresponding peptides. Thus, it is conceptually possible to assemble an entire rational-designed collection of (neo)epitopes of a specific patient with a specific cancer, which can then be further tested in vitro to find or generate high-affinity receptors. In one aspect of the inventive subject matter, one or more of the peptide (neo)epitopes (e.g., 9-mers) can be immobilized on a solid carrier (e.g., magnetic or color coded bead) and used as a bait to bind surface presented receptor fragments. Numerous libraries for T cell receptors are known in the art and suitable in conjunction with the teachings presented herein. Where desired, smaller libraries may also be used and be subjected to affinity maturation to improve binding affinity and/or kinetic using methods well known in the art (see e.g., Briefings in functional genomics and proteomics. Vol 1. No 2. 189-203. July 2002). In addition, it should be noted that while libraries are generally preferred, other scaffolds are also deemed suitable and include beta barrels, ribosome display, cell surface display, etc. (see e.g., Protein Sci. 2006 January; 15(1): 14-27.) In addition, as already discussed above, it should be appreciated that not only patient and tumor specific neoepitopes are deemed suitable, but also all known tumor associated antigens (e.g., CEACAM, MUC-1, HER2, etc.) as well as various self-lipids.

In some embodiments, the nucleic acid encoding T cell receptor complex may be identified from the patient in need of therapy or may be obtained from a donor. That is, they may be autologous or allogeneic. Routine tests well known to those of skill in the art may be used to identify allogeneic T cell receptor complexes using routine HLA compatibility analyses, e.g. HLA A, B, DR, etc. to identify any desired level of compatibility. As such, the presently described methods allow for providing genetically modified NK cells capable of supplementing a patient's own T cell response from a donor. Methods of determining HLA compatibility are described by Howell, *J Clin Pathol.* 2010; 63(5):387-90; and "The HLA system: immunobiology, HLA typing, antibody screening and crossmatching techniques," *Clin Transl Med.* 2013; 2:6. HLA typing is commercially available from Linkage Biosciences, South San Francisco, California.

Without wishing to be bound by any specific theory, the inventors contemplate that the genetically modified immunocompetent cells such as NK cells expressing the T cell receptor complex that specifically recognize a cancer (neo) epitope increase the T cell immune response (e.g., cytotoxicity against the tumor cells), against the tumor by tumor-specific targeting. In addition, as more T cells are recruited near the tumor, the T cells are expected to alter the microenvironment of the tumor via their immunesurveillance function (e.g., by locally releasing cytokines, etc.).

The recombinant nucleic acids can be introduced into immunocompetent cells such as NK cells by any suitable means. Preferably, the recombinant nucleic acid can be inserted into a suitable vector to be introduced to and expressed in the NK cells. The suitable vector includes, but not limited to, any mammalian cell expression vector and a viral vector, depending on the methodology of introducing the recombinant nucleic acid to the cells. Alternatively, where the recombinant nucleic acid(s) is/are RNA, the nucleic acid may be transfected into the cells. It should also be recognized that the manner of recombinant expression is not limited to a particular technology so long as the modified cells are capable of producing the chimeric protein in a constitutive or inducible manner. Therefore, the cells may be transfected with linear DNA, circular DNA, linear RNA, a DNA or RNA virus harboring a sequence element encoding the chimeric protein, etc. Viewed form a different perspective, transfection may be performed via ballistic methods, virus-mediated methods, electroporation, laser poration, lipofection, genome editing, liposome or polymer-mediated transfection, fusion with vesicles carrying recombinant nucleic acid, etc.

Thus, it should also be appreciated that the recombinant nucleic acid may be integrated into the genome (via genome editing or retroviral transfection) or may be present as a stable or transient extrachromosomal unit (which may have replicating capability). For example, the recombinant nucleic acid that is used to transfect the cytotoxic cell may be configured as a viral nucleic acid and suitable viruses to transfect the cells include adenoviruses, lentiviruses, adeno-associated viruses, parvoviruses, togaviruses, poxviruses, herpes viruses, etc. Alternatively, the recombinant nucleic acid may also be configured as extrachromosomal unit (e.g., as plasmid, yeast artificial chromosome, etc.), or as a construct suitable for genome editing (e.g., suitable for CRiPR/Cas9, Talen, zinc-finger nuclease mediated integration), or may be configured for simple transfection (e.g., as RNA, DNA (synthetic or produced in vitro), PNA, etc.). Therefore, it should also be noted that the cells may be transfected in vitro or in vivo.

The inventors further contemplate that the immunocompetent cells such as NK cells to be genetically modified with the recombinant nucleic acids described above can be ex vivo expanded NK cells depending on the desired immune response against the tumor cells or tumor microenvironment. For example, NK cells may be expanded with interferons or macrophage-derived cytokines.

Administration of NK Cells to a Patient Having a Tumor

The inventors also contemplate that ex vivo expanded and optionally activated genetically modified NK cells can be administered to a patient having a tumor or cancer (or suffering from a viral infection such as a retroviral infection). It is contemplated that the NK cells (e.g., isolated, isolated and ex vivo expanded, genetically modified, etc.) and/or genetically engineered NK cells can be formulated in any pharmaceutically acceptable carrier (e.g., as a sterile injectable composition) with a cell titer of at least $1\times10^3$ cells/ml, preferably at least $1\times10^5$ cells/ml, more preferably at least $1\times10^6$ cells/ml, and at least 1 ml, preferably at least 5 ml, more preferably and at least 20 ml per dosage unit. However, alternative formulations are also deemed suitable for use herein, and all known routes and modes of administration are contemplated herein. As used herein, the term "administering" genetically NK cells and/or genetically modified NK cells refers to both direct and indirect administration of the NK cells and/or genetically modified NK cells formulation, wherein direct administration of NK cells and/or genetically modified NK cells is typically performed by a health care professional (e.g., physician, nurse, etc.), and wherein indirect administration includes a step of providing or making available the NK cells and/or genetically modified NK cell formulation to the health care professional for direct administration (e.g., via injection, etc.).

While the composition can comprise only genetically modified NK cells, it is also contemplated that the composition can comprise a mixture of naive NK cells and genetically modified NK cells. In this composition, the ratio of naive NK cells and genetically modified NK cells may vary based on the type of cancer, age, gender, or health status of the patient, size of tumor, or NK cell counts in the patient's blood. In some embodiments, the ratio of genetically modified NK cells and NK cells is at least 1:1, at least 2:1, at least 3:1, at least 5:1, or at least 1:2, at least 1:3, or at least 1:5.

In some embodiments, the NK cells and/or genetically modified NK cell formulation is administered via systemic injection including subcutaneous, subdermal injection, or intravenous injection. In other embodiments, where the systemic injection may not be efficient (e.g., for brain tumors, etc.), it is contemplated that the NK cells and/or genetically modified NK cell formulation is administered via intratumoral injection.

With respect to dose of the genetically modified NK cell formulation administration, it is contemplated that the dose may vary depending on the status of disease, symptoms, tumor type, size, location, patient's health status (e.g., including age, gender, etc.), and any other relevant conditions. While it may vary, the dose and schedule may be selected and regulated so that the NK cells and/or genetically modified NK cells do not provide any significant toxic effect to the host normal cells, yet sufficient to be effective to induce an cytotoxic effect and/or immune-modulatory effect against the tumor and/or the tumor microenvironment such that size of the tumor is decreased (e.g., at least 5%, at least 10%, at least 20%, etc.), the number of tumor cells is decreased, the phenotype of the tumor may be changed (e.g., shape, change in gene expression, change in protein expression, change in post-translational modification of a protein, etc.), the accumulation of MDSC and/or Tregs may be prevented (or stopped, decreased, etc.).

With respect to the schedule of administration, it is contemplated that it may also vary depending on the status of disease, symptoms, tumor type, size, location, patient's health status (e.g., including age, gender, etc.), and any other relevant conditions. In some embodiments, a single dose of NK cells and/or genetically modified NK cell formulation can be administered at least once a day or twice a day (half dose per administration) for at least a day, at least 3 days, at least a week, at least 2 weeks, at least a month, or any other desired schedule. In other embodiments, the dose of the NK cells and/or genetically modified NK cell formulation can be gradually increased during the schedule, or gradually decreased during the schedule. In still other embodiments, several series of administration of NK cells and/or genetically modified NK cell formulation can be separated by an interval (e.g., one administration each for 3 consecutive days and one administration each for another 3 consecutive days with an interval of 7 days, etc.).

In some embodiments, the administration of the genetically modified NK cell formulation can be in two or more different stages: a priming administration and a boost administration. It is contemplated that the dose of the priming administration is higher than the following boost administrations (e.g., at least 20%, preferably at least 40%, more preferably at least 60%). Yet, it is also contemplated that the dose for priming administration is lower than the following boost administrations. Additionally, where there is a plurality of boost administration, each boost administration has different dose (e.g., increasing dose, decreasing dose, etc.).

In some embodiments, the dose and schedule of the genetically modified NK cell formulation administration may be fine-tuned and informed by cellular changes of the infected cells or cancer cells. For example, after a cancer patient is administered with one or more dose of genetically modified NK cell formulation, a small biopsy of the cancer tissue may be obtained in order to assess any changes (e.g., upregulation of NKG2D ligand, apoptosis rate, etc.) resulted from interaction with the genetically modified NK cell formulation. The assessment of cellular changes can be performed by any suitable types of technology, including immunohistochemical methods (e.g., fluorescence labeling, in-situ hybridization, etc.), biochemical methods (e.g., quantification of proteins, identification of post-translational modification, etc.), or omics analysis. Based on the result of the assessment, the dose and/or schedule of the genetically modified NK cell formulations can be modified (e.g., lower dose if excessive cytotoxicity is observed, etc.).

Pretreatment to Tumor to Increase Effectiveness of NK Cell Immune Response

Genetically modified NK cells are activated upon recognition of MHC class I-antigen complex on the antigen presenting cells to elicit immune response against the antigen presenting cells by releasing multiple cytokines and chemokines (such as IL-2, Interleukin-13, Interleukin-17, Interleukin-21, and TNF-alpha). Thus, in addition to administering genetically modified NK cells to the patient, preferably to the tumor or tumor microenvironment, pre-conditioning of the tumor to promote a condition in which the tumor is more susceptible to administered NK cells is especially contemplated.

For example, in some embodiments, the tumor cells can be preconditioned to genetically modified NK cell-susceptible (or responsive) conditions and followed by in vivo expansion of genetically modified NK cells. In such embodiments, the genetically modified NK cells can be expanded by applying (preferably locally applying near the tumor) activating molecules, including but not limited to, cytokines (e.g., IL-2, IL-5, IL-7, IL-8, IL-12, IL-12, IL-15, IL-18, and IL-21, preferably human recombinant IL-2, IL-5, IL-7, IL-8, IL-12, IL-12, IL-15, IL-18, and IL-21, etc.) in any desirable concentration (e.g., at least 10 U/ml, at least 50 U/ml, at least 100 U/ml), T cell receptor antibodies (e.g., anti-CD2, anti-CD3, anti-CD28, α-TCR-Vα24+ antibodies, preferably immobilized on beads, etc.), a glycolipid (e.g., α-GlcCer, etc.), a glycolipid coupled with CD1 (e.g., CD1d, etc.). The amount of in vivo expanded genetically modified NK cells can be determined by counting the genetically modified NK cells from a biopsy tissue or from a locally collected bodily fluid.

While any suitable conditions that can increase the susceptibility or responsiveness of the cancer cells to the genetically modified NK cells are contemplated, it is most preferred that the tumor cells are treated with a condition to express a universally recognized antigen such as a CD1 or CD1 coupled with a peptide or lipid antigen on the cell surface. In some embodiments, a recombinant nucleic acid encoding the universally recognized antigen (wild-type or modified) can be introduced to the cancer cells so that the universally recognized antigen molecule is overexpressed in the tumor. Preferably, the recombinant nucleic acid encoding the universally recognized antigen is inserted into a viral genome and introduced to the cancer cells. Any suitable virus to carry recombinant nucleic acid encoding the universally recognized antigen is contemplated. The suitable virus include oncolytic virus, preferably genetically modified oncolytic virus presenting low immunogenicity to the host. For example, a preferred oncolytic virus includes genetically modified adenovirus serotype 5 (Ad5) with one or more deletions in its early 1 (E1), early 2b (E2b), or early 3 (E3) gene (e.g., E1 and E3 gene-deleted Ad5 (Ad5[E1]), E2b gene-deleted Ad5 (Ad5[E1,E2b], etc.). In one preferred virus strains having Ad5 [E1-, E2b-] vector platform, early 1 (E1), early 2b (E2b), and early 3 (E3) gene regions encoding viral proteins against which cell mediated immunity arises, are deleted to reduce immunogenicity. Also, in this strain, deletion of the Ad5 polymerase (pol) and preterminal protein (pTP) within the E2b region reduces Ad5 downstream gene expression which includes Ad5 late genes that encode highly immunogenic and potentially toxic proteins. Viewed from a different perspective and among other suitable viruses, particularly preferred oncolytic viruses include non-replicating or replication deficient adenoviruses.

Preferably, a recombinant nucleic acid encoding a universally recognized antigen such as CD1 includes a nucleic acid segment encoding a signaling peptide that directs the universally recognized antigen to the cell surface. Any suitable and/or known signaling peptides are contemplated (e.g., leucine rich motif, etc.). Preferably, the nucleic acid segment encoding the universally recognized antigen is located in the upstream of the nucleic acid segment encoding signaling peptide such that the signal sequence can be located in C-terminus of the antigen. However, it is also contemplated that the signaling peptide can be located in the N-terminus of or in the middle of the universally recognized antigen such as CD1.

Additionally, the recombinant nucleic acid encoding a universally recognized antigen such as CD1 may include a nucleic acid segment encoding a peptide ligand of universally recognized antigen such as CD1 (e.g., a hydrophobic short peptide), for example, p99. In this embodiment, the recombinant nucleic acid may include a first nucleic acid segment encoding universally recognized antigen such as CD1 and a second nucleic acid segment encoding p99, and the first and second nucleic acid segments are separated by a nucleic acid sequences encoding a type of 2A self-cleaving peptide (2A) so that the universally recognized antigen such as CD1 and p99 can be translated into two separate and distinct peptide, yet the expression of two peptides can be regulated under the same promoter. The inventors contemplate that the co-expressed universally recognized antigen such as CD1 and p99 are coupled intracellularly, trafficked together to the tumor cell surface, and trigger genetically modified NK cell activation when the genetically modified NK cell recognizes the tumor cells via universally recognized antigen such as CD1 receptor interaction or MHC-epitope-T cell receptor (or CAR) interaction. It should be noted that in at least some instances, p99 may be bound to universally recognized antigen such as CD1 in an unorthodox manner that may disrupt conventional T cell recognition. However, as p99 appears to be a strong ligand with physiological signaling capability, other interactions (with T cells or other immune competent cells) are also contemplated herein.

Alternatively, the tumor cells can be further treated with one or more genetically modified NK cell agonists including, but not limited to, α-GalCer, β-mannosylceramide (β-ManCer), or GD3 (melanoma-derived ganglioside). In this embodiment, α-GalCer, β-ManCer, GD3, or any combination of those, can be locally applied (e.g., intratumorally injected, etc.) after the recombinant nucleic acid encoding universally recognized antigen such as CD1 is introduced to the tumor cells (e.g., at least 1 day after, at least 3 days after, at least 7 days after, etc.). The inventors contemplate that the surface-expressed universally recognized antigen such as CD1 binds to extracellular α-GalCer, β-ManCer, or GD3 to form a CD1-α-GalCer complex, a CD1-β-ManCer complex, or CD1-GD3 complex and trigger genetically modified NK cell activation when the genetically modified NK cell recognizes the tumor cells via universally recognized antigen such as CD1 receptor interaction or MHC-(neo)epitope-T cell receptor (or CAR) interaction. In an embodiment where multiple types of extracellular genetically modified NK cell agonists are treated to the tumor cells, it is contemplated that the extracellular genetically modified NK cell agonists can be treated sequentially (e.g., α-GalCer in day 1, β-ManCer in day 3, and GD3 in day 5, etc.). Yet, it is also contemplated that the multiple extracellular genetically modified NK cell agonists can be treated as a cocktail to the tumor cells for a single treatment or for multiple treatments.

In other embodiments, the tumor cells can be subjected to conditions or pretreated with any composition that can stress the tumor cells to increase expression of a tumor associated antigen. For example, local heat shock treatment (e.g., at 42 degree celcius for 1 min, for 3 min, for 5 min, etc.), hypoxia, chemotherapy, exposure to toxins, low dose radiation, and/or mechanical damage (e.g., partial surgical removal of cancer tissue, etc.).

Supplementing or Augmenting a T cell Response

The genetically modified NK cells and methods described herein allow treating a patient that supplements and augments the T cell response already occurring. T cell populations recognizing particular antigens, neoepitopes or self-lipids may over time become exhausted with a prolonged response. The exhaustion of a prolonged T cell immune response is readily observable by measuring certain exhaustion markers. A population of genetically modified NK cells may be administered to a patient to supplement, augment or maintain the T cell immune response of an already exhausted T cell population. A discussion of T cell exhaustion is provided by Wherry, "T Cell Exhaustion," *Nature Immunology* 2011; 12:492-499; Xi, *Cell Commun Signal* 2017; 15: 1; and Pauken et al., "Overcoming T cell Exhaustion in Infection and Cancer," *Trends in Immunology,* 2015; 36(4):265-276, the disclosures of which are herein incorporated by reference. As such, the nucleic acid sequences encoding the T cell receptor may be chosen from identified exhausted T cell populations in the patient.

The inventors transfected control natural killer NK-92 cells with mRNA encoding GFP to verify transfection efficiency and transfected other natural killer NK-92 cells with mRNA encoding the T cell receptor mRNA encoding a T cell receptor α chain separated by a 2A sequence followed by mRNA encoding a T cell receptor β chain and with a second T cell receptor RNA encoding a T cell receptor γ chain followed by a 2A sequence and another mRNA encoding a T cell receptor δ chain. The transfected NK cells were contacted with dendritic cells infected with *Tuberculosis mycobacterium* expressing CD1b surface antigen as an antigen presenting cell in conjunction with the antigen mycolic acid. The transfected NK cells recognized the mycolic acid antigen thereby demonstrating that the transfected NK cells were expressing a functional T cell receptor.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A genetically engineered natural killer (NK) cell for augmenting an anti-tumor T cell response in a subject, comprising:
    a recombinant nucleic acid encoding a protein complex having an α chain T cell receptor, a β chain T cell receptor, at least a portion of CD3δ, and at least a portion of CD3δ; wherein at least a portion of the α chain T cell receptor or the β chain T cell receptor is specific to a patient-specific neoepitope;
    wherein the α chain T cell receptor and the β chain T cell receptor have a sequence that is identical to an α chain T cell receptor and a β chain T cell receptor of an exhausted T cell of the subject; and
    wherein the portion of CD3γ or CD3δ comprises an immunoreceptor tyrosine-based activation motif (ITAM).

2. The genetically engineered natural killer cell of claim 1, wherein the recombinant nucleic acid comprises:
    a first nucleic acid segment encoding the α chain T cell receptor and the β chain T cell receptor, the α and β chain receptor being separated by a first self-cleaving 2A peptide sequence; and
    a second nucleic acid segment encoding at least a portion of CD3δ and at least a portion of CD3γ, the at least a portion of CD3δ and the at least a portion of CD3γ being separated by a second self-cleaving 2A peptide sequence.

3. The genetically engineered natural killer cell of claim 2, wherein the first nucleic acid segment and the second nucleic acid segment are separated by a third self-cleaving 2A peptide sequence.

4. The genetically engineered natural killer cell of claim 2, wherein the natural killer cell is generated from a NK-92 derivative cell.

5. A pharmaceutical composition for treating a patient having a tumor or a cancer, comprising a plurality of the genetically engineered natural killer cells of claim 1.

* * * * *